(12) United States Patent
Chandar et al.

(10) Patent No.: US 7,361,364 B2
(45) Date of Patent: Apr. 22, 2008

(54) COSMETIC COMPOSITION

(75) Inventors: Prem Chandar, Trumbull, CT (US); Vinodkumar Ramniranjan Dhanuka, Mumbai (IN); Vibhav Ramrao Sanzgiri, Mumbai (IN); Shivani Kiran Shah, Atlanta, GA (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 11/363,345

(22) Filed: Feb. 27, 2006

(65) Prior Publication Data

US 2006/0239955 A1   Oct. 26, 2006

(30) Foreign Application Priority Data

| Feb. 28, 2005 | (IN) | ............ 0216/MUM/2005 |
| Jun. 9, 2005 | (EP) | ............ 05253529 |
| Jun. 25, 2005 | (GB) | ............ 0513005.9 |

(51) Int. Cl.
*A61K 8/02* (2006.01)

(52) U.S. Cl. .................... 424/401; 424/400
(58) Field of Classification Search ............ 424/70.31, 424/400, 401
See application file for complete search history.

(56) References Cited

U.S. PATENT DOCUMENTS

| 5,270,054 | A | 12/1993 | Bertolini et al. |
| 5,759,524 | A | 6/1998 | Tanner et al. |
| 5,827,508 | A | 10/1998 | Tanner et al. |
| 5,851,544 | A | 12/1998 | Penska et al. |
| 6,136,771 | A | 10/2000 | Taylor et al. |
| 2003/0163877 | A1* | 9/2003 | Baker et al. .............. 8/405 |
| 2003/0206979 | A1 | 11/2003 | Dvoracek et al. |
| 2005/0112074 | A1 | 5/2005 | Arai et al. |

FOREIGN PATENT DOCUMENTS

| EP | 1 224 928 | 7/2002 |
| IN | 190820 | 8/2003 |
| WO | 01/74311 | 11/2001 |
| WO | 2004/100904 | 11/2004 |
| WO | 2005/039517 | 5/2005 |

* cited by examiner

*Primary Examiner*—Shelley A. Dodson
(74) *Attorney, Agent, or Firm*—Edward A. Squillante, Jr.; Ellen Plotkin

(57) ABSTRACT

A cosmetic composition is provided which is substantially free of fatty acids and soap and yet displays the typical sensory and optical features of a vanishing cream. The composition comprises $C_{12}$-$C_{22}$ fatty alcohol, emulsifier, inorganic agent, polymer and water. The inorganic agent comprises smectite clay. The composition is mild and may be used to stabilise and deliver a wide variety of skin benefit agents such as sunscreens.

13 Claims, No Drawings

COSMETIC COMPOSITION

TECHNICAL FIELD OF THE INVENTION

The present invention relates to a mild cosmetic base composition that may be used to deliver benefit agents to the skin. In particular the present invention relates to a mild cosmetic base composition that provides sensory characteristics of a vanishing cream. The present invention also relates to a cosmetic composition for topical application comprising a mild cosmetic base that provides sensory characteristics of a vanishing cream.

BACKGROUND TO THE INVENTION

Cosmetic compositions to deliver benefit agents are prepared by combining various oils and vehicles using various emulsifying systems.

Many consumers desire cosmetic products that have unique tactile properties during use and post-use. Specifically, such products should, upon application to the skin, deliver a high skin friction and a matte finish to overcome the oily skin feel and shiny skin appearance. The greater the increase in skin friction, the less greasy the user perceives the product to be. Vanishing cream bases which generally comprise fatty acids and alkali metal soaps are one of the preferred forms of such a cosmetically acceptable vehicle especially by consumers living in hot, humid climates, or consumers with oily skin.

More specifically, the typical sensory and optical features of these high skin friction and matte finish creams (vanishing creams) are to: 1) provide a dry, draggy, non-greasy, non-sticky feel to skin; 2) provide a non-shiny, matte finish; 3) spread easily on the skin; 4) absorb or "vanish" rapidly into the skin.

The traditionally used vanishing creams contain high levels of stearic acid and alkaline metal soap as an emulsifier, both of which are important to the physical stability & sensory properties of the product. The soap is usually formed by in-situ neutralization of a part of the total stearic acid with caustic potash or other alkali.

Unfortunately, however, many benefit agents e.g. acidic actives and sunscreens, are not chemically and physically stable in such vanishing creams that are largely based on fatty acids.

IN 190820, U.S. Pat. Nos. 5,827,508 and 5,759,524 (all to The Procter & Gamble Company) disclose photo-protective cosmetic compositions where in order to improve the chemical and photo stability of sunscreens, special materials such as surface treated zinc oxide are incorporated in the formulation. Whilst such formulations may be substantially free of fatty acids, unfortunately they lack the above-mentioned desirable sensory properties of a vanishing cream.

Thus we have identified that there is a need for a cosmetic base composition, which is free of stearic acid or other fatty acids and soap and yet maintains the sensory characteristics of a vanishing cream base. We have found that such a goal may be achieved by the careful selection of inorganic and organic agents emulsified with suitable emulsifier(s) and formulated with polymers.

It is thus an object of the present invention to formulate a cosmetic composition that is substantially free of fatty acids and soap and yet capable of providing the sensory characteristics of a vanishing cream.

It is another object of the present invention to formulate a cosmetic composition that is free of fatty acids and soap and is milder than a vanishing cream while providing the sensory characteristics of a vanishing cream.

It is yet another object of the present invention to formulate a cosmetic composition that is free of fatty acids and soap and in which a wide variety of benefit agents can be incorporated and that can stabilize benefit agents such as sunscreens and other acidic actives while providing the sensory characteristics of a vanishing cream.

It is yet another object of the present invention to formulate a cosmetic composition that is capable of enhancing the efficacy of both UV-A and UV-B types of sunscreen.

BRIEF DESCRIPTION OF THE INVENTION

According to the present invention there is provided a cosmetic composition substantially free of fatty acids and soap, and comprising:

i. 3-10% by weight of the composition of a fatty alcohol with a carbon chain length $C_{12}$-$C_{22}$;
ii. 0.1 to 5% by weight of the composition of an emulsifier;
iii. 2 to 5% by weight of the composition of an inorganic agent comprising smectite clay;
iv. 0.1 to 5% by weight of the composition of a polymer; and
v. at least 65% water by weight of the composition.

In order to maximise the mildness of the composition and increase its propensity for stabilising skin benefit agents, it is preferable that the cosmetic composition comprises less than 5% total fatty acids and soap by weight of the composition, more preferably less than 2%, even more preferably less than 0.5% and optimally less than 0.1%.

It is also preferred that the melting point of the emulsifier used is at least 35° C.

Water is the preferred solvent and incorporated preferably at a level of 65 to 85% by weight of the composition. Other solvents can be incorporated in addition to water at a level of between 0.5 to 10% by weight of the composition. Examples of suitable solvents include: propylene glycol, polyethylene glycol, polypropylene glycol, glycerol, 1,2,4-butanetriol, 1,2,6-hexanetriol, ethanol, isopropanol, sorbitol esters, butanediol, acetone, ethylene glycol monoethyl ether, diethylene glycol monobutyl ether, diethylene glycol monoethyl ether and mixtures thereof.

The composition according to the invention can also be used as a cosmetically acceptable vehicle to act as a diluent, dispersant or carrier for other materials. The composition according to the invention can be used to formulate cosmetic compositions by incorporating benefit agents useful for topical application, so as to facilitate their distribution when the composition is applied to the skin. These benefit agents can comprise a wide range of cosmetic and pharmaceutical ingredients commonly used in the skin care industry, which are suitable for use in the compositions of the present invention. These materials can be incorporated at levels not exceeding 20% (by weight of the composition) in their native (anhydrous) state and can be incorporated singly or with mixtures of one or more vehicles or emulsions (including oil-in-water, water-in-oil or water-in-oil-in-water emulsions).

DETAILED DESCRIPTION OF THE INVENTION

Preferred components suitable for inclusion in the cosmetic composition of the present invention are now described in detail.

Fatty Alcohol:

Suitable fatty alcohols are generally selected from those with a carbon chain length $C_{12}$-$C_{22}$. It is preferred that at least 50% by weight of the fatty alcohol is a straight chain fatty alcohol. It is particularly preferred that the fatty alcohol is a saturated fatty alcohol. It is also particularly preferred that at least 50% of the total fatty alcohols, by weight of fatty alcohol, are solid at a temperature of at least 35° C.

Particularly preferred is one or a combination of fatty alcohols selected from stearyl, cetyl, or cetostearyl alcohol.

The total concentration of the fatty alcohol is in the range from 3 to 10% by weight of the cosmetic composition and more preferably from 4 to 7%.

Emulsifier:

The emulsifier used in the composition comprises non-soap detergents and is free of soap. The emulsifier is preferably selected from anionic or nonionic surfactants. The total concentration of the emulsifier is in the range from 0.1 to 5% by weight of the composition, preferably from 1 to 4%. It is particularly preferred that the melting point of the emulsifier(s) used is at least 35° C.

Non-limiting examples of anionic surfactants are alkyl sulfates, aralkyl sulfates, alkyl ethoxy ether sulfates, alkaryl sulfates, alkyl succinates, alkyl sulfosuccinates (including mono- and dialkyl, e.g., $C_6$-$C_{22}$ sulfosuccinates), n-alkoyl sarcosinates, isethionates, and taurates.

Non-limiting examples of non-ionic emulsifiers include glyceryl esters, ethylene glycol esters, propylene glycol esters and sucrose esters of fatty acids, such as: glyceryl caprate, glyceryl lanolate, glyceryl myristate, glyceryl laurate, glyceryl dilaurate, glyceryl monostearate, glyceryl monohydroxy stearate, glyceryl stearate SE, glyceryl stearate citrate, glycol stearate, glycol distearate, glycol dilaurate, diethylene glycol dilaurate, propylene glycol stearate, propylene glycol laurate, propylene glycol distearate, palm glycerides, hydrogenated coco glycerides, sucrose distearate.

Another useful class of non-ionic emulsifers is polyethylene esters of fatty acids, fatty acid glycerides and sorbitan esters and with ethylene groups ranging from 5 to 150. Examples include: PEG-8 stearate, PEG-9 stearate, PEG-8 distearate, PEG-20 stearate, PEG-30 stearate, PEG-40 stearate, EG-50 stearate, PEG-100 stearate, PEG-150 laurate, PEG-30 glyceryl stearate, PEG-25 glyceryl trioleate, PEG-15 glyceryl ricinoleate, PEG-20 glyceryl stearate, PEG-20 glyceryl isostearate, PEG-20 glyceryl oleate, PEG-20 glyceryl laurate, PEG-30 stearate, PEG-30 glyceryl stearate, PEG-40 sorbitan lanolate, PEG-6 sorbitan beeswax and PEG-20 sorbitan beeswax.

Yet another useful class of non-ionic emulsfiers is represented by ethoxylated fatty alcohols with ethylene groups ranging from 2 to 30.

Other non-ionic emulsfiers may include sorbitan monoesters like sorbitan stearate, sorbitan tristearate, sorbitan palmitate, sorbitan laurate, cholesterol, lanolin, phytosterols, lecithin and hydrogenated lecithin.

Inorganic Agents:

Inorganic agents with or without organic modifications are part of the composition. The total amount of these agents in the composition is in the range from 2 to 5% by weight of the composition. The inorganic agent comprises smectite clay. Preferably at least 20% by weight of the inorganic agent is a smectite clay, more preferably at least 30%, even more preferably at least 40% and optimally at least 50%.

Preferably the smectite clay is chosen from the group consisting of: aluminum silicates, such as the montmorillonites (bentonites, hectorites and derivatives thereof); purified magnesium aluminum silicates (commercially available as Veegum™ in various grades); purified sodium magnesium silicates (commercially available as Laponite™ in various grades); organically modified smectites including tetra alkyl and/or trialkyl ammonium smectites (organically modified montmorillonite clays) such as quaternium-18 bentonite, quaternium-18 hectorite, stearalkonium bentonite and stearalkonium hectorite; and mixtures thereof.

Montmorillonites represent clay minerals, which belong to the dioctahedral smectites, and are materials which swell in water but do not become plastic. The layer packets in the 3-layer structure of the montmorillonites can swell as the result of reversible incorporation of water (in a 2-7 fold amount) and other substances, such as, for examples, alcohols, glycols, pyridine, α-picoline, ammonium compounds, hydroxyaluminosilicate ions, etc.

Since montmorillonite has a large capacity for ion exchange, aluminum can be replaced by Mg, Fe(II), Fe(III), Zn, Pb, Cr, Cu and others. The resulting negative charge of the octahedral layers is balanced by cations, in particular $Na^+$ (sodium montmorillonite) and $Ca^{2+}$ (calcium montmorillonite) in interlayer positions.

The organophilization of montmorillonite or bentonites (exchange of the interlayer cations for quaternary alkylammonium ions) produces products (bentones), which are also useful herein.

The balance of the inorganic agent may be selected individually or as mixtures from the following: silicas, silicates, colloidal silicas, silicate pigments in which the free —OH groups on the surface of the particles have been (completely or partially) organically modified, chalk, talc, kaolin, Fullers earth, sodium polyacrylate, chemically modified magnesium aluminum silicate, hydrated aluminum silicate, zinc oxide, titanium oxide, and mixtures thereof.

Polymers:

The total concentration of the polymer is in the range from 0.1 to 5% by weight of the composition and preferably from 0.3 to 2%.

Suitable polymers may be selected from the following classes of thickeners/gelling agents: acrylamides, taurates, cross-linked polyacrylate polymers, acrylic acid co-polymers, polysaccharides, starch (including modified starches) and hydrocolloids.

Preferred polymers are those selected from the group consisting of carboxylic acid polymers, cross-linked polyacrylate polymer, polyacrylamide polymers and mixtures thereof. More preferred polymers are those selected from the group consisting of cross-linked polyacrylate polymers, polyacrylamide polymers and mixtures thereof. See U.S. Pat. No. 4,387,107 (Kelin et al., issued Jun. 7, 1983) and "Encyclopedia of Polymers and Thickeners for Cosmetics", R. Y. Lochhead and W. R. Fron, Eds., Cosmetics and Toileteries, Vol 108, pp 95-135 (May 1993), which list a variety of polymers, thickening and/or gelling agents and which are all incorporated herein by reference in their entirety.

Carboxylic Acid Polymers:

Examples of commercially available carboxylic acid polymers useful herein include the carbomers, which are homopolymers of acrylic acid cross-linked with allyl ethers of sucrose or pentaerytritol. These carbomers are commercially available as the Carbopol™ 900 series from B. F. Goodrich. Another type of commercially available carboxylic acid polymer useful herein include copolymers of $C_{10}$-$C_{30}$ alkyl acrylates with one or more monomers of acrylic acid, methacrylic acid, or one of their short chain (i.e. $C_1$-$C_4$ alcohol) esters, wherein the cross-linking agent is an allyl ether of sucrose or pentaerythritol. These co-polymers are known as acrylates/$C_{10}$-$C_{30}$ alkyl acrylate cross-polymers and are commercially available as Carbopol™ 342, Pemulen™ TR-1 and Pemulen™ TR-2 from B. F. Goodrich. Thus, preferred examples of carboxylic acid polymers useful herein are those selected from the group consisting of carbomers, acrylates/$C_{10}$-$C_{30}$ alkyl acrylate crosspolymers, and mixtures thereof.

Polyacrylamide Polymers:

Also useful herein are polyacrylamide polymers, especially non-ionic polyacrylamide polymers including substituted branched or un-branched polymers. Most preferred among these polyacrylamide polymers are the non-ionic polymers given the CTFA designation polyacrylamide and isoparaffin and laureth-7 available under the trade name Sepigel™ 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan™ SR150H, SS500V, SS500W, SSSA100H, from Lipo Chemicals Incorporated (Patterson, N.J.). Also advantageous for the purposes of the present invention are compounds which have the INCI name ammonium acryloyldimethyltaurate/vinylpyrrolidone copolymers and which have the empirical formula $[C_7H_{16}N_2SO_4]_n$ $[C_6H_9NO]_m$. Preferred species for the purposes of the present invention are listed in the Chemical Abstracts under the registry numbers 58374-69-9, 13162-05-5 and 88-12-0 and are available under the trade name Aristoflex™ AVC from Clariant GmbH. Also advantageous are copolymers/ crosspolymers comprising acryloyl dimethyl taurate, such as, for example, Simugel™ EG from Seppic Corporation.

Polysaccharides:

A wide variety of polysaccharides are useful herein. By "polysaccharides" are meant (gelling) agents containing a backbone of repeating sugar (i.e. carbohydrate) units. Non-limiting examples of polysaccharides include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer are hydroxyalkylated (preferably hydroxyethylated or hydroxypropylated) to form a hydroxyalkylated cellulose, which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (e.g. alkyl groups derived from the alcohols of coconut oil), palmityl, oleyl, linoleyl, linolenyl, ricinoleyl, behenyl, and mixtures thereof.

Preferred among the alykyl hydroxyalkyl cellulose ethers is the material given the CTFA designation cetyl hydroxyethylcellulose, which is the ether of cetyl alcohol and hydroxyethylcellulose. This material is sold under the trade name Natrosol™ CS Plus from Aqualon Corporation.

Other additional polymers/thickening/gelling agents useful herein include materials which are primarily derived from natural sources. Non-limiting examples of these agents include starch and starch derivatives, materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum and mixtures thereof.

Hydrocolloids:

"Hydrocolloid" is the technological abbreviation for the more correct name "hydrophilic colloid". Hydrocolloids are macromolecules, which have a largely linear structure and have intramolecular forces of interaction which permit secondary and primary valence bonds between the individual molecules and thus the formation of reticular structures. Such water-soluble polymers represent a large group of chemically very different natural and synthetic polymers whose common feature is their solubility in water or aqueous media. A prerequisite for this is that these polymers have a large number of hydrophilic groups sufficient for solubility in water and not too greatly cross-linked. The hydrophilic groups may be non-ionic, anionic or cationic in nature.

Optional Skin Benefit Agents and Feel Modifiers:

Suitable additional skin benefit agents including sunscreens, anti-aging, wrinkle-reducing, skin whitening/lightening, anti-blemish, anti-irritants, anti-acne, and sebum/oil reduction agents, moisturizing agents, humectants, skin-softening agents as well as feel modifiers such as oils, emollients, silicones, modified inorganic and organic particulates, etc. and aromatherapy agents and perfumes may be included in the composition.

Emollients and oils include but are not limited to stearyl alcohol, glyceryl monoricinoleate, cetyl alcohol, isopropyl isostearate, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, squalane, squalene, cholesterol, butyl myristate, isopropyl linoleate, lauryl lactate, myristyl lactate, decyl oleate, myristyl myristate; and mixtures thereof etc.

Non-limiting examples of silicone oils include polydimethylsiloxanes, cyclomethicones, phenyltrimethicone, dimethiconol and mixtures thereof.

Humectants can be selected from a non-limiting list of glycerin, diglycerin, triglycerin, polyglycerin, ethoxylated and propoxylated glycerols, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, and mixtures thereof.

Sunscreens:

By topical application to the skin of a mixture of inorganic sunscreens or sunblock agents and/or organic sunscreens, synergistically enhanced protection of the skin against the harmful effects of both UV-A and UV-B rays is achievable.

The one or more sunscreen agents that can be used in the present invention must be capable of absorbing or blocking the harmful effects of ultraviolet radiation. In addition, they must be non-toxic and non-irritating when applied to the skin.

Non-limiting examples of suitable sunscreen agents that may be used in the sunscreen composition include, for example, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine) boran-2-one (methylbenzindinecamphor), benzotriazole, phenylbenzimidazole-5-sulfonic acid, methylene bis-benzotrizolyl tetramethylbutyl phenol, and mixtures thereof.

Useful inorganic sunscreens (or sun-blocks) include, but are not limited to, zinc oxide, iron oxide, silica, such as fumed silica, and titanium dioxide. The total amount of inorganic sunscreen that is preferably incorporated in the composition according to the invention is from 0.1 to 5% by weight of the composition.

Ultrafine titanium dioxide is especially suitable for the present invention, and may be in either of its two forms, namely water-dispersible titanium dioxide and oil-dispersible titanium dioxide.

Water-dispersible titanium dioxide is ultra-fine titanium dioxide, the particles of which are non-coated or which are coated with a material to impart a hydrophilic surface property to the particles. Examples of such materials include aluminium oxide and aluminium silicate. Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

The amount of one or more sunscreen agent(s) in the composition will vary in the above range depending on the sun protection factor (SPF) or tan protection index (TPI) desired. The higher the SPF/TPI, the greater the total amount of sunscreen agent.

The preferred sunscreen agents are avobenzone, benzophenone-3, octyl methoxycinnamate, octyl salicylate, homosalate, zinc oxide, octocrylene, avobenzone, titanium dioxide, and mixtures thereof.

The following examples are by way of example, not by way of limitation, of the principles of the present invention, to illustrate the best mode of carrying out the invention.

EXAMPLES i. Sensory Studies:

A formulation according to the invention (Example A), along with identical formulations but without polymer and/or inorganic agent (Comparative Examples 1, 2 and 3) as described in Table 1, were compared with a conventional vanishing cream base (Comparative Example 4) for key vanishing cream-like sensory characteristics. Formulations were unstable when emulsifiers were not included and so could not be tested in the sensory studies.

The study was conducted using a 15 member expert panel of trained women who used a known amount of the test formulations as described in Table 1 and compared it to the conventional vanishing cream. The panelists were given coded samples in a randomized order. Panelists gave their comments on the sensory attributes of the formulations both during use and after use. Each panelist scored each formulation on a set of attributes (as indicated in Table 2) using a scale of 1 to 10. Each panelist was regularly validated using control formulations which were used to define the scales for each attribute, e.g. for greasiness the scale ranged from 1 (completely non-greasy like water) to 10 (very greasy/heavy like petroleum jelly).

TABLE 1

| Composition (% wt) | Comparative Example 1 | Comparative Example 2 | Comparative Example 3 | Example A | Comparative Example 4 |
|---|---|---|---|---|---|
| Stearic acid | — | — | — | — | 17.9 |
| Stearyl alcohol | 5 | 5 | 5 | 5 | 0.5 |
| Soap (formed in-situ by addition of KOH to the stearic acid) | — | — | — | — | 2.5 |
| Glyceryl hydroxy stearate (2%) + sodium cetearyl sulphate (0.3%) | 2.3 | 2.3 | 2.3 | 2.3 | — |
| Sepigel ™* | — | — | 0.5 | 0.5 | — |
| Veegum ™** (1%) + titanium dioxide*** (1.2%) | — | 2.2 | — | 2.2 | — |
| Sunscreens**** | 1.15 | 1.15 | 1.15 | 1.15 | 1.15 |
| Water | to 100 | to 100 | to 100 | to 100 | to 100 |
| Consistency of the formulation | Not a cream***** | Cream | Cream | Cream | Cream |

*Polyacrylamide and isoparaffin and laureth-7 available under the trade name Sepigel ™ 305 from Seppic Corporation (Fairfield, NJ).
**Aluminum silicate sold, for example by R. T. Vanderbilt Company Incorporated, under the trade name Veegum ™.
***MT-100SA from the TAYCA Company.
****0.75% Parsol MCX + 0.4% Parsol 1789 supplied by Chemspec/Roche.
*****Comparative Example 1 was not evaluated, as it was not a cream.

TABLE 2

| Sensory parameter | Comparative Example 2 | Comparative Example 3 | Example A | Comparative Example 4 |
|---|---|---|---|---|
| In-Use Properties | | | | |
| Creamy Feel | 5.53 | 5.79 | 5.21 | 5.37 |
| Greasiness | 2.95 | 4.95 | 3.37 | 3.42 |
| Stickiness | 2.79 | 5.16 | 3.32 | 3.58 |
| Thickness | 5.84 | 4.53 | 5.16 | 5.00 |
| Wet Feel | 2.74 | 4.79 | 3.42 | 3.05 |
| Skin Temp (Cooling) | 2.89 | 3.16 | 2.95 | 2.95 |
| Ease Of Spreading | 6.74 | 7.32 | 6.84 | 6.95 |
| Absorption Rate | 7.00 | 7.21 | 6.89 | 6.89 |
| Soft Feel | 6.37 | 6.95 | 6.79 | 6.84 |
| Post-use properties | | | | |
| Final Greasiness | 1.84 | 3.37 | 2.00 | 2.53 |
| Final Stickiness | 1.89 | 3.11 | 2.00 | 2.37 |
| Smoothness (Not Draggy) | 6.68 | 7.32 | 5.79 | 5.84 |
| Shine (Not Matte) | 1.26 | 3.32 | 1.47 | 2.00 |

A higher score means a stronger affirmation of the sensory character described, i.e. a score of 1.84 on Final greasiness means less greasy end-feel than a cream having a score of 3.11 (more greasy end-feel). The parameters of Smoothness and Shine are opposing parameters to desired properties of Draggy and Matte feel. Hence a lower score on Smoothness indicates more Draggy while a lower score on Shine indicates more Matte.

As the data above in Table 2 clearly shows, only the formulation according to the invention (Example A) shows an almost complete match with a high stearic acid vanishing cream (Comparative Example 4), while elimination of emulsifier or polymer or inorganic agents does not provide the same effect.

ii. Mildness:

To test the mildness of the cosmetic base composition according to the invention (Example A) against a standard vanishing cream (Comparative Example 4), a multiple exposure patch test method was used. For this study 24 multi-ethnic panelists (both males and females) were used. The upper outer aspect of the arm was exposed once for 24 hours followed by a maximum of three 18 hour exposures at the same site, using standard 25 mm Hill-Top Chambers fitted with 18 mm Webril padding and held in place with a non-irritating tape. 0.2 ml (200 mg) of the test material was applied to the padding just prior to application. Test sites were graded for level of irritation (combination Draize irritation scale) 6 hours after patch removal. Test sites were also ranked in order of severity at that time. The most severe site was given Rank 1 followed by the milder formulation in order of increasing ranks (2, 3, 4, etc.). If the irritation at a site exceeds a cumulative score of 2, the sites were not patched again. Analysis of the mildness was done using the sum of the cumulative ranks (a higher score is indicative of a milder formulation) as well as based on the number of panelists discontinued. The data are presented in Table 3.

TABLE 3

| | Comparison of sum of ranks | | Panelists discontinued | |
|---|---|---|---|---|
| Day | Example A | Comparative Example 4 | Example A | Comparative Example 4 |
| 3 | 144.0 | 114.5 | 3 | 4 |
| 4 | 132.0 | 112.0 | 5 | 12 |

The above results clearly demonstrate that the cosmetic base composition according to the invention (Example A) is milder than the corresponding vanishing cream base formulation (Comparative Example 4).

iii. Improvement in Sunscreen Stability and Efficacy:

It is known that sunscreen stability (particularly that of octylmethoxycinnamate and uncoated zinc oxide) is adversely affected in high stearic acid containing formulations.

To assess the impact of compositions according to the invention in improving the stability and related efficacy of the sunscreens, both in-vitro and in-vivo studies were carried out.

SPF measurement: In-vitro Sun Protection Factor (SPF) was measured 21 days after manufacture. Product films were drawn on quartz plates using a 37 micron metal coating draw-down tool and allowed to dry in the dark for 30 mins. The absorbance of the film on a specific spot on the plate was read from a wavelength of 290 nm to 400 nm using a SPF 290 (Optometrics USA Incorporated) The spot was continuously irradiated and 10 readings taken at 90 s intervals. The change in absorbance at 300 nm from the initial to the final scan was used as a measure of sunscreen stability in the formulation (i.e. % of initial absorbance=100* asborbance @ 300 nm (scan 10)/absorbance at 300 nm (scan 1)). Three preparations were made per formulation, and an average SPF value taken. The details of the formulations and the measure of sunscreen stability are presented in Table 4.

TABLE 4

| Composition % wt | Example B | Example C | Comparative Example 5 |
|---|---|---|---|
| Stearic acid | — | — | 17.9 |
| Stearyl alcohol | 5 | 5 | 0.5 |
| Emulsifier* | 2.3 | 2.3 | 2.5 (Soap) |
| Polymer** | 0.5 | 0.5 | — |
| Inorganic agent (Veegum ™ (1%) + Silica spheres (1.2%) or Anatase (1.2%)) | 2.2 (Anatase) | 2.2 (Silica Spheres) | — |
| Parsol MCX | 0.75 | 0.75 | 0.75 |
| Benzophenone-3 | 0.4 | 0.4 | 0.4 |
| Micronized $TiO_2$*** | 0.2 | 0.2 | 0.2 |
| Water | to 100 | to 100 | to 100 |
| % of initial absorbance (Measure of stability) | 91.5% | 76.0% | 16.5% |

*Glyceryl hydroxy stearate (2%) + sodium cetearyl sulphate (0.3%).
**Ammonium acryloyldimethyltaurate/Vinylpyrrolidone available under the trade name Aristoflex ™ AVC from Clariant GmbH.
***MT-100Z from the TAYCA Company.

The above results clearly demonstrate that cosmetic compositions according to the invention (Examples B and C) show greater stability of the sunscreens (largely UV-B type) as compared to a conventional vanishing cream base (Comparative Example 5).

Tanning study: This study was designed to evaluate the tan protection efficacy (largely on account of the UV-A component) of sunscreens. The study followed double blind design in which both study personnel and study subjects were not aware of test product composition. Both forearms (area from elbow to wrist) were selected for treatment and the formulations and respective controls and untreated sites were maintained. Sites were exposed to the mid-day sun for 30 min and clinically/visually evaluated prior to application and immediately after exposure on the first day. The evaluation was performed by expert graders using a tanning scale with clear qualitative descriptors of the various manifestations/extent of tanning. The application and sun exposure continued for 3 consecutive days. As melanogenesis usually peaks around 5 to 7 days following exposure, the sites were visually evaluated for tan up to 10 days. On the tenth day, post visual evaluation, a tan protection index or TPI [(Grade of tan level on untreated site—Grade of tan level on treated site)/Grade of tan level on untreated site] was calculated. The greater the TPI value, the better the tan protection (i.e, less is the tanning seen).

Table 5 shows the composition of the formulations tested in this study and the results of the tanning protection seen on the tenth day.

TABLE 5

| Composition % wt. | Example D | Example E | Comparative Example 6 | Comparative Example 7 |
|---|---|---|---|---|
| Stearic acid | — | — | 17.9 | 17.9 |
| Stearyl alcohol | 5 | 5 | 0.5 | 0.5 |
| Emulsifier* | 2.3 | 2.3 | 2.5 (Soap) | 2.5 (Soap) |
| Polymer (Aristoflex™ AVC) | 0.5 | 0.5 | — | — |
| Clay-minerals (Veegum™ (1%) + Silica spheres (1.2%)) | 2.2 | 2.2 | — | — |
| Parsol MCX | 0.75 | 0.75 | 0.75 | 0.75 |
| Parsol 1789 | 0.4 | 0.4 | 0.4 | 0.4 |
| Micronized TiO$_2$** | 0.2 | 0.2 | 0.2 | 0.2 |
| Zinc Oxide (Nanox™ 200) | — | 1 | — | 1 |
| Water | to 100 | to 100 | to 100 | to 100 |
| TPI Score | 0.81 | 0.84 | 0.24 | 0.26 |

*Glyceryl hydroxy stearate (2%) + sodium cetearyl sulphate (0.3%).
**MT-100Z from the TAYCA Company.

The results show that a composition according to the invention (Example D) with the same sunscreens as a conventional vanishing cream (Comparative Example 6) shows significantly improved tanning protection. The results also show that the same trend is reproduced for formulations (Example E and Comparative Example 7) to which uncoated 60 nm diameter zinc oxide sunscreen (Nanox™ 200) were added. The results for both Example D and Example E clearly demonstrate that improved sunscreen efficacy is achieved with compositions according to the invention as compared to a vanishing cream base.

The invention claimed is:

1. A cosmetic composition substantially free of fatty acids and soap, and comprising:
    $C_{12}$-$C_{22}$ fatty alcohol in an amount of 3 to 10% by weight of the composition;
    emulsifier in an amount of from 0.1 to 5% by weight of the composition;
    inorganic agent in an amount of from 2 to 5% by weight of the composition, and comprising smectite clay;
    polymer in an amount of from 0.1 to 5% by weight of the composition; and
    water in an amount of at least 65% by weight of the composition,
    the cosmetic composition being one which provides sensory characteristics of a vanishing cream after topical application.

2. The cosmetic composition according to claim 1 wherein the amount of fatty alcohol is from 4 to 7% by weight of the composition.

3. The cosmetic composition according to claim 1 wherein at least 50% by weight of the fatty alcohol is straight chain fatty alcohol.

4. The cosmetic composition as claimed in claim 1 wherein the fatty alcohol comprises saturated fatty alcohol.

5. The cosmetic composition as claimed in claim 1 wherein the emulsifier has a melting point of at least 35° C.

6. The cosmetic composition as claimed in claim 1 wherein the emulsifier is selected from anionic surfactant, nonionic surfactant, and mixtures thereof.

7. The cosmetic composition as claimed in claim 1 wherein the amount of emulsifier is from 1 to 4% by weight of the composition.

8. The cosmetic composition as claimed in claim 1 wherein at least 20% by weight of the inorganic agent is smectite clay.

9. The cosmetic composition as claimed in claim 1 wherein the smectite clay is selected from the group consisting of montmorillonites, bentonites, hectorites, purified magnesium aluminium silicates, purified sodium magnesium silicates, organically modified smectites, and mixtures thereof.

10. The cosmetic composition as claimed in claim 1 wherein the amount of polymer is from 0.3 to 2%.

11. The cosmetic composition according to claim 1 wherein the cosmetic composition is suitable to stabilize one or more skin benefit agents.

12. The cosmetic composition according to claim 1 wherein the cosmetic composition is suitable to enhance the efficacy of one or more sunscreens.

13. The cosmetic composition according to claim 1 wherein the cosmetic composition is suitable to deliver one or more skin benefit agents to the skin of an individual.

* * * * *